United States Patent [19]

Antos

[11] 4,295,959

[45] Oct. 20, 1981

[54] HYDROCARBON DEHYDROCYCLIZATION WITH AN ATTENTUATED SUPERACTIVE MULTIMETALLIC CATALYTIC COMPOSITE

[75] Inventor: George J. Antos, Bartlett, Ill.

[73] Assignee: UOP Inc., Des Plaines, Ill.

[21] Appl. No.: 198,733

[22] Filed: Oct. 20, 1980

Related U.S. Application Data

[60] Continuation-in-part of Ser. No. 48,957, Jun. 15, 1979, Pat. No. 4,229,319, which is a division of Ser. No. 954,684, Oct. 25, 1978, Pat. No. 4,206,040, which is a continuation-in-part of Ser. No. 833,332, Sep. 14, 1977, Pat. No. 4,165,276.

[51] Int. Cl.$^3$ .................. C07C 15/8; B01J 27/08; C10G 35/09
[52] U.S. Cl. .................. 208/138; 208/139; 585/415; 585/419
[58] Field of Search ............... 585/415, 419; 208/139

[56] References Cited

U.S. PATENT DOCUMENTS

| | | | |
|---|---|---|---|
| 2,620,314 | 12/1952 | Hoekstra | 252/448 |
| 2,892,858 | 6/1959 | Ziegler | 260/448 |
| 3,415,737 | 12/1968 | Kluksdahl | 208/139 |
| 3,661,805 | 5/1972 | Horvath | 252/465 |
| 3,725,249 | 4/1973 | Vesely et al. | 208/139 |
| 3,852,190 | 12/1974 | Buss et al. | 208/138 |
| 3,933,622 | 1/1976 | Mitchell et al. | 252/441 |
| 4,012,313 | 3/1977 | Buss et al. | 208/139 |
| 4,085,157 | 4/1978 | Juguin et al. | 585/419 |
| 4,229,319 | 10/1980 | Antos | 252/441 |

Primary Examiner—Delbert E. Gantz
Assistant Examiner—G. E. Schmitkons
Attorney, Agent, or Firm—James R. Hoatson, Jr.; Louis A. Morris; William H. Page, II

[57] ABSTRACT

Dehydrocyclizable hydrocarbons are converted to aromatics by contacting them at hydrocarbon dehydrocyclization conditions with an attenuated superactive acidic multimetallic catalytic composite comprising a combination of a catalytically effective amount of a pyrolyzed rhenium carbonyl component with a porous carrier material containing catalytically effective amounts of a halogen component, a silver component and a uniform dispersion a catalytically effective amount of a platinum group component which is maintained in the elemental metallic state. The platinum group, pyrolyzed rhenium carbonyl, silver and halogen components are present in the multimetallic catalyst in amounts respectively, calculated on an elemental basis, corresponding to about 0.01 to about 2 wt. % platinum group metal, about 0.01 to about 5 wt. % rhenium, about 0.01 to about 5 wt. % silver and about 0.1 to about 3.5 wt. % halogen. A specific example of a dehydrocyclization method disclosed herein is a method for converting a feed mixture of n-hexane and n-heptane to a product mixture of benzene and toluene which involves contacting the feed mixture and a hydrogen stream with the attenuated superactive acidic multimetallic catalyst disclosed herein at hydrocarbon dehydrocyclization conditions.

25 Claims, No Drawings

HYDROCARBON DEHYDROCYCLIZATION WITH AN ATTENTUATED SUPERACTIVE MULTIMETALLIC CATALYTIC COMPOSITE

CROSS-REFERENCE TO RELATED APPLICATIONS

This application is a continuation-in-part of my prior, copending application and issued Ser. No. 48,957 filed June 15, 1979 as U.S. Pat. No. 4,229,319; which in turn is a division of my prior application Ser. No. 954,684 filed Oct. 25, 1978 and issued June 3, 1980 as U.S. Pat. No. 4,206,040; which in turn is a continuation-in-part of my prior application Ser. No. 833,332 filed Sept. 14, 1977 and issued Aug. 21, 1979 as U.S. Pat. No. 4,165,276. All of the teachings of these prior applications are specifically incorporated herein by reference.

The subject of the present invention is, broadly, an improved method for dehydrocyclizing a dehydrocyclizable hydrocarbon to produce an aromatic hydrocarbon. In a narrower aspect, the present invention involves a method of dehydrocyclizing aliphatic hydrocarbons containing 6 to 20 carbon atoms per molecule to monocyclic aromatic hydrocarbons with minimum production of side products such as $C_1$ to $C_5$ hydrocarbons, bicyclic aromatics, olefins and coke. In another aspect, the present invention relates to the dehydrocyclization use of an attenuated superactive acidic multimetallic catalytic composite comprising a combination of a catalytically effective amount of a pyrolyzed rhenium carbonyl component with a porous carrier material containing a platinum group metal component, a silver component and a halogen component. This attenuated superactive acidic multimetallic composite has been found to possess highly beneficial characteristics of activity, selectivity, and stability when it is employed in the dehydrocyclization of dehydrocyclizable hydrocarbons to make aromatics such as benzene, toluene and xylene.

The conception of the present invention followed from my search for a novel catalytic composite possessing a hydrogenation-dehydrogenation function, a controllable cracking and isomerization function, and superior conversion, selectivity, and stability characteristics when employed in hydrocarbon conversion processes that have traditionally utilized dual-function catalytic composites. In my prior application Ser. No. 954,684, I disclosed a significant finding with respect to a multimetallic catalytic composite meeting these requirements. More specifically, I determined that a pyrolyzed rhenium carbonyl component can be utilized, under certain conditions, to beneficially interact with the platinum group and silver components of a dual-function acidic catalyst with a resultant marked improvement in the performance of such a catalyst. Now I have ascertained that an acidic multimetallic catalytic composite, comprising a combination of a pyrolyzed rhenium carbonyl component with a porous carrier material containing a platinum group metal, silver and a halogen component, can have superior activity, selectivity, and stability characteristics when it is employed in a hydrocarbon ring-closure or dehydrocyclization process.

The dehydrocyclization of dehydrocyclizable hydrocarbons is an important commercial process because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well-known to those skilled in the art. One example of this demand is in the manufacture of alkylated aromatics such as ethylbenzene, cumene and dodecylbenzene by using the appropriate mono-olefins to alkylate benzene. Another example of this demand is in the area of chlorination of benzene to give chlorobenzene which is then used to prepare phenol by hydrolysis with sodium hydroxide. The chief use for phenol is of course in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene by selective dehydrogenation; styrene is in turn used to make styrene-butadiene rubber and polystyrene. Ortho-xylene is typically oxidized to phthalic anhydride by reaction in vapor phase with air in the presence of a vanadium pentoxide catalyst. Phthalic anhydride is in turn used for production of plasticizers, polyesters and resins. The demand for para-xylene is caused primarily by its use in the manufacture of terephthalic acid or dimethylterephthalate which in turn is reacted with ethylene glycol and polymerized to yield polyester fibers. Substantial demand for benzene also is associated with its use to produce aniline, Nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed a number of alternative methods to produce them in commercial quantities. One method that has been widely studied involves the selective dehydrocyclization of a dehydrocyclizable hydrocarbon by contacting the hydrocarbon with a suitable catalyst at dehydrocyclization conditions. As is the case with most catalytic procedures, the principal measure of effectiveness for this dehydrocyclization method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the specific reaction conditions used—that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously the smaller rate implying the more stable catalyst. More specifically, in a dehydrocyclization process, activity commonly refers to the amount of conversion that takes place for a given dehydrocyclizable hydrocarbon at a specified severity level and is typically measured on the basis of disappearance of the dehydrocyclizable hydrocarbon; selectivity is typically measured by the amount, calculated on a weight percent of feed basis or on a mole percent of converted dehydrocyclizable hydrocarbon basis, of the desired aromatic hydrocarbon or hydrocarbons obtained at the particular activity or severity level; and stability is typically equated to the rate of change with time of activity as measured by disappearance of the dehydrocyclizable hydrocarbon and of selectivity as measured by the amount of desired aromatic hydrocarbon produced. Accordingly, the major problem facing workers in the hydrocarbon dehydrocyclization or ring-closure art is the development of a more active and selective catalytic composite that has good stability characteristics.

I have now found a dual-function acidic multimetallic catalytic composite which possesses improved activity, selectivity, and stability when it is employed in a process for the dehydrocyclization of dehydrocyclizable hydrocarbons. In particular, I have determined that the use of an attenuated superactive acidic multimetallic catalyst, comprising a combination of a catalytically effective amount of a pyrolyzed rhenium carbonyl component with a porous carrier material containing catalytically effective amounts of a platinum group component, a silver component and a halogen component, can enable the performance of a hydrocarbon dehydrocyclization process to be substantially improved if the platinum group component is relatively uniformly dispersed throughout the porous carrier material prior to contact with the rhenium carbonyl component, if the oxidation state of the platinum group component is maintained in the elemental metallic state prior to and during contact with the rhenium carbonyl component and if high temperature treatment of the resulting reaction product with oxygen and/or water is avoided. This attenuated superactive acidic multimetallic catalytic composite is particularly useful in the dehydrocyclization of $C_6$ to $C_{10}$ paraffins to produce aromatic hydrocarbons such as benzene, toluene, and the xylenes with minimization of by-products such as $C_1$ to $C_5$ saturated hydrocarbons, bicyclic aromatics, olefins and coke.

In sum, the current invention involves the significant finding that a pyrolyzed rhenium carbonyl component can be utilized under the circumstances specified herein to beneficially interact with and promote an acidic hydrocarbon dehydrocyclization catalyst containing a platinum group metal and silver when it is used in the production of aromatics by ring-closure of aliphatic hydrocarbons.

It is, accordingly, one object of the present invention to provide a novel method for the dehydrocyclization of dehydrocyclizable hydrocarbons utilizing an attenuated superactive acidic multimetallic catalytic composite comprising catalytically effective amounts of platinum group component, a pyrolyzed rhenium carbonyl component, a silver component and a halogen component combined with a porous carrier material. A second object is to provide a novel attenuated superactive acidic catalytic composite having superior performance characteristics when utilized in a hydrocarbon dehydrocyclization process. Another object is to provide an improved method for the dehydrocyclization of paraffin hydrocarbons to produce aromatic hydrocarbons which method minimizes undesirable by-products such as $C_1$ to $C_5$ saturated hydrocarbons, bicyclic aromatics, olefins and coke.

In brief summary, one embodiment of the present invention involves a method for dehydrocyclizing a dehydrocyclizable hydrocarbon which comprises contacting the hydrocarbon at hydrocarbon dehydrocyclization conditions with an attenuated superactive acidic multimetallic catalytic composite comprising a combination of a catalytically effective amount of a pyrolyzed rhenium carbonyl component with a porous carrier material containing catalytically effective amounts of a halogen component, a silver component and a uniform dispersion of a catalytically effective amount of a platinum group component maintained in the elemental metallic state.

A second embodiment relates to the dehydrocyclization method described in the first embodiment wherein the dehydrocyclizable hydrocarbon is an aliphatic hydrocarbon containing 6 to 20 carbon atoms per molecule.

A highly preferred embodiment comprehends the dehydrocyclization method characterized in the first embodiment wherein the catalyst contains the components in amounts, calculated on an elemental basis corresponding to about 0.01 to about 2 wt. % platinum group metal, about 0.01 to about 5 wt. % rhenium, about 0.01 to about 5 wt. % silver and about 0.1 to about 3.5 wt. % halogen.

Another embodiment relates to the catalytic composite used in the first, second or third embodiments and involves the further limitation that the halogen component is chlorine.

Other objects and embodiments of the present invention involves specific details regarding essential and preferred catalytic ingredients, preferred amounts of ingredients, suitable methods of multimetallic composite preparation, suitable dehydrocyclization hydrocarbons, operating conditions for use in the dehydrocyclization process, and the like particulars. There are hereinafter given in the following detailed discussion of each of these facets of the present invention.

Regarding the dehydrocyclizable hydrocarbon that is subjected to the method of the present invention, it can in general be any aliphatic hydrocarbon or substituted aliphatic hydrocarbon capable of undergoing ring-closure to produce an aromatic hydrocarbon. That is, it is intended to include within the scope of the present invention, the dehydrocyclization of any organic compound capable of undergoing ring-closure to produce an aromatic hydrocarbon containing the same, or less than the same, number of carbon atoms than the reactant compound and capable of being vaporized at the dehydrocyclization temperatures used herein. More particularly, suitable dehydrocyclizable hydrocarbons are: aliphatic hydrocarbons containing 6 to 20 carbon atoms per molecule such as $C_6$ to $C_{20}$ paraffins, $C_6$ to $C_{20}$ olefins and $C_6$ to $C_{20}$ polyolefins. Specific examples of suitable dehydrocyclizable hydrocarbons are: (1) paraffins such as n-hexane, 2-methylpentane, 3-methylpentane, 2,2-dimethylbutane, n-heptane, 2-methylhexane, 3-ethylpentane, 2,2-dimethylpentane, n-octane, 2-methylheptane, 3-ethylhexane, 2,2-dimethylhexane, 2-methyl-3-ethylpentane, 2,2,3-trimethylpentane, n-nonane, 2-methyloctane, 2,2-dimethylheptane, n-decane and the like compounds; (2) olefins such as 1-hexene, 2-methyl-1-pentene, 1-heptene, 1-octene, 1-nonene and the like compounds; and, (3) diolefins such as 1,5-hexadiene, 2-methyl-2,4-hexadiene, 2,6-octadiene and the like diolefins.

In a preferred embodiment, the dehydrocyclizable hydrocarbon is a paraffin hydrocarbon having about 6 to 10 carbon atoms per molecule. For example, paraffin hydrocarbons containing about 6 to 8 carbon atoms per molecule are dehydrocyclized by the subject method to produce the corresponding aromatic hydrocarbon. It is to be understood that the specific dehydrocyclizable hydrocarbons mentioned above can be charged to the present method individually, in admixture with one or more of the other dehydrocyclizable hydrocarbons, or in admixture with other hydrocarbons such as naphthenes, aromatics, $C_1$ to $C_5$ paraffins and the like. Thus mixed hydrocarbon fractions, containing significant quantities of dehydrocyclizable hydrocarbons that are commonly available in a typical refinery, are suitable charge stocks for the instant method; for example, highly paraffinic straight run naphthas, paraffinic raffinates from aromatic extraction or adsorption, $C_6$ to $C_9$ paraffin-rich streams and the like refinery streams. An especially preferred embodiment involves a charge stock which is a paraffin-rich naphtha fraction boiling in the range of about 140° to about 400° F. Generally, best results are obtained with a charge stock comprising a mixture of $C_6$ to $C_9$ paraffins, and especially $C_6$ to $C_9$ normal paraffins.

The acidic multimetallic catalyst used in the present dehydrocyclization method comprises a porous carrier material having combined therewith catalytically effective amounts of a platinum group component, a pyrolyzed rhenium carbonyl component, a silver component and a halogen component.

Considering first the porous carrier material utilized in the present invention, it is preferred that the material be a porous adsorptive, high-surface area support having a surface area of about 25 to about 500 $m^2/g$. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc., (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $CaAl_2O_4$, and other like compounds having the formula $MO.Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume is about 0.1 to about 1 cc/g and the surface area is about 100 to about 500 $m^2/g$. In general, bests results are typically obtained with a gamma-alumina carrier material which is used in the form of spherical particles having: a relatively small diameter (i.e. typically about 1/16 inch), an apparent bulk density of about 0.3 to about 0.8 g/cc, a pore volume of about 0.4 ml/g, and a surface area of about 150 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well-known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gama-alumina. See the teachings of U.S. Pat. No. 2,620,314 for additional details.

Another particularly preferred alumina carrier material is synthesized from a unique crystalline alumina powder which has been characterized in U.S. Pat. Nos. 3,852,190 and 4,012,313 as a by-product from a Ziegler higher alcohol synthesis reaction as described in Ziegler's U.S. Pat. No. 2,892,858. For purposes of simplification, the name "Ziegler alumina" is used herein to identify this material. It is presently avaiable from the Conoco Chemical Division of Continental Oil Company under the trademark Catapal. This material is an extremely high purity alpha-alumina monohydrate (boehmite) which after calcination at a high temperature has been shown to yield a high purity gamma-alumina. It is commercially available in three forms: (1) Catapal SB—a spray dried powder having a typical surface area of 250 m²/g; (2) Catapal NG—a rotary kiln dried alumina having a typical surface area of 180 m²/g; and (3) Dispal M—a finely divided dispersible product having a typical surface area of about 185 m²/g. For purposes of the present invention, the preferred starting material is the spray dried powder, Catapal SB. This alpha-alumina monohydrate powder may be formed into a suitable catalyst material according to any of the techniques known to those skilled in the catalyst carrier material forming art. Spherical carrier material particles can be formed, for example, from this Ziegler alumina by: (1) converting the alpha-alumina monohydrate powder into an alumina sol by reaction with a suitable peptizing acid and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disc until spherical particles are formed which can then be dried and calcined to form the desired particles of spherical carrier material; and (3) wetting the powder with a suitable peptizing agent and thereafter rolling particles of the powder into spherical masses of the desired size in much the same way that children have been known to make parts of snowmen by rolling snowballs down hills covered with wet snow. This alumina powder can also be formed in any other desired shape or type of carrier material known to those skilled in the art such as rods, pills, pellets, tablets, granules, extrudates and the like form by methods well known to the practitioners of the catalyst carrier material forming art. The preferred type of carrier material for the present invention is a cylindrical extrudate having a diameter of about 1/32" to about ⅛" (especially about 1/16") and a length to diameter (L/D) ratio of about 1:1 to about 5:1, with a L/D ratio of about 2:1 being especially preferred. The especially preferred extrudate form of the carrier material is preferably prepared by mixing the alumina powder with water and a suitable peptizing agent such as nitric acid, acetic acid, aluminum nitrate and the like material until an extrudable dough is formed. The amount of water added to form the dough is typically sufficient to give a loss on ignition (LOI) at 500° C. of about 45 to 65 wt. %, with a value of about 55 wt. % being especially preferred. On the other hand, the acid addition rate is generally sufficient to provide about 2 to 7 wt. % of the volatile free alumina powder used in the mix, with a value of about 3 to 4% being especially preferred. The resulting dough is then extruded through a suitably sized die to form extrudate particles. It is to be noted that it is within the scope of the present invention to treat the extrudable dough with an aqueous alkaline reagent such as an aqueous solution of ammonium hydroxide prior to extrusion of same as specified in the teachings of U.S. Pat. No. 3,661,805. These particles are then dried at a temperature of about 500° to 800° F. for a period of about 0.1 to about 5 hours and thereafter calcined at a temperature of about 900° F. to about 1500° F. for a period of about 0.5 to about 5 hours to form the preferred extrudate particles of the Ziegler alumina carrier material. In addition, in some embodiments of the present invention the Ziegler alumina carrier material may contain minor proportions of other well-known refractory inorganic oxides such as silica, titanium dioxide, zirconium dioxide, chromium oxide, beryllium oxide, vanadium oxide, cesium oxide, hafnium oxide, zinc oxide, iron oxide, cobalt oxide, magnesia, boria, thoria, and the like materials which can be blended into the extrudable dough prior to the extrusion of same. In the same manner crystalline zeolitic aluminosilicates such as naturally occurring or synthetically prepared mordenite and/or faujasite, either in the hydrogen form or in a form which has been treated with a multivalent cation, such as a rare earth, can be incorporated into this carrier material by blending finely divided particles of same into the extrudable dough prior to extrusion of same. A preferred carrier material of this type is substantially pure Ziegler alumina having an apparent bulk density (ABD) of about 0.6 to 1 g/cc (especially an ABD of about 0.7 to about 0.85 g/cc), a surface area of about 150 to about 280 m²/g (preferably about 185 to about 235 m²/g), and a pore volume of about 0.3 to about 0.8 cc/g.

A first essential ingredient of the subject catalyst is the platinum group component. That is, it is intended to cover the use of platinum, iridium, osmium, ruthenium, rhodium, palladium, or mixtures thereof as a first component of the superactive catalytic composite. It is an essential feature of the present invention that substantially all of this platinum group component is uniformly dispersed throughout the porous carrier material in the elemental metallic state prior to the incorporation of the rhenium carbonyl ingredient. Generally, the amount of this component present in the form of catalytic composites is small and typically will comprise about 0.01 to about 2 wt. % of final catalytic composite, calculated on an elemental basis. Excellent results are obtained when the catalyst contains about 0.05 to about 1 wt. % of platinum, iridium, rhodium or palladium metal. Particularly preferred mixtures of these platinum group metals preferred for use in the composite of the present invention are: (1) platinum and iridium and (2) platinum and rhodium.

This platinum group component may be incorporated in the porous carrier material in any suitable manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water soluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium or palladium chloride compound, such as chloroplatinic, chloroiridic, or chloropalladic acid or rhodium trichloride hydrate, is preferred since it facilitates the incorporation of both the platinum group component and at least a minor quantity of the preferred halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum group compound.

A second essential constituent of the multimetallic catalyst of the present invention is a silver component. This component may in general be present in the instant catalytic composite in any catalytically available form such as the elemental metal or a compound like the oxide, hydroxide, halide, oxyhalide, aluminate, sulfide, or in chemical combination with one or more of the other ingredients of the catalyst. Although it is not intended to restrict the present invention by this explanation, it is believed that best results are obtained when the silver component is present in the composite in a form wherein substantially all of the silver moiety is in the elemental metallic state, and the subsequently described oxidation and reduction steps that are preferably used in the preparation of the instant catalytic composite are specifically designed to achieve this end. This silver component can be used in any amount which is catalytically effective, with good results obtained, on an elemental basis, with about 0.01 to about 5 wt. % silver in the catalyst. Best results are ordinarily achieved with about 0.01 to about 1 wt. % silver, calculated on an elemental basis, and with an atomic ratio of silver to platinum group metal of about 0.1:1 to about 10:1, especially about 0.5:1 to about 3:1.

This silver component may be incorporated into the porous carrier material in any suitable manner known to the art to result in a relatively uniform dispersion of the silver moiety in the carrier material, such as by coprecipitation or cogelation or coextrusion with the porous carrier material, ion exchange with the gelled carrier material, or impregnation with the carrier material either after, before, or during the period when it is dried and calcined. It is to be noted that it is intended to include within the scope of the present invention all conventional methods for incorporating and simultaneously uniformly distributing a metallic component in a catalytic composite and the particular method of incorporation used is not deemed to be an essential feature of the present invention. One preferred method of incorporating the silver component into the porous carrier material involves cogelling or coprecipitating or coextruding the silver component in the form of the corresponding hydrous oxide or chloride during the preparation of the preferred carrier material, alumina. This method typically involves the addition of a suitable sol-soluble or sol-dispersible silver compound such as silver nitrate or chlorate to the alumina hydrosol and then combining the hydrosol with a suitable gelling agent and forming the resulting mixture into particles of appropriate size and shape such as by dropping the resulting mixture into an oil bath, etc., as explained in detail hereinbefore. Alternatively, the silver compound can be added to the gelling agent. After drying and calcining the resulting gelled carrier material in air, there is obtained an intimate combination of alumina and silver. Another preferred method of incorporating the silver component into the porous carrier material involves utilization of a soluble, decomposable compound of silver to impregnate the porous carrier material. In general, the solvent used in this impregnation step is selected on the basis of the capability to dissolve the desired silver compound without adversely affecting the carrier material or the other ingredients of the catalyst—for example, water, a suitable alcohol, ether, acid and the like solvents. The solvent is preferably an aqueous solution. Thus, the silver component may be added to the carrier material by commingling the latter with an aqueous solution of suitable silver salt, complex, or compound such as silver acetate, chlorate, perchlorate, fluoride, nitrate, and the like compounds. A particularly preferred impregnation solution comprises an aqueous solution of silver nitrate. In general, the silver component can be impregnated either prior to, simultaneously with, or after the platinum group component is added to the carrier material. However, excellent results are obtained when the silver component is added to the porous carrier material prior to the addition of the rhenium carbonyl component.

It is especially preferred to incorporate a halogen component into the platinum group metal and silver-containing porous carrier material prior to the reactions thereof with the rhenium carbonyl reagent. Although the precise form of the chemistry of the association of the halogen component with the catalytic composite is not entirely known, it is customary in the art to refer to the halogen component as being combined with the carrier material or with the platinum group and/or silver components in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or during or after the addition of the platinum group and silver components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group and/or silver components, for example, through the utilization of a mixture of chloroplatinic acid and hydrogen chloride. In another situation, the alumina hydrosol which is typically utilized to form a preferred alumina carrier material may contain halogen and thus contribute at least a portion of the halogen component to the final composite. For dehydrocyclization, the halogen will be typically combined with the carrier material in an amount sufficient to result in a final composite that contains about 0.1 to about 3.5%, and preferably about 0.5 to about 1.5% by weight of halogen, calculated on an elemental basis.

It is to be understood that the specified level of halogen component in the instant superactive catalyst can be achieved or maintained during the use in the dehydrocyclization or hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm of the hydrocarbon feed, and preferably about 1 to 10 wt. ppm.

After the platinum group component is combined with the porous carrier material, the resulting platinum group metal containing carrier material will generally be dried at a temperature of about 200° F. to about 600° F. for a period of typically about 1 to about 24 hours or more and thereafter oxidized at a temperature of about 700° F. to about 1100° F. in an air or oxygen atmosphere for a period of about 0.5 to about 10 or more hours or converts substantially all of the platinum group component to the corresponding platinum group oxide. When the preferred halogen component is utilized in the present composition, best results are generally obtained when the halogen content of the platinum group metal-containing carrier material is adjusted during this oxidation step by including a halogen or a halogen-containing compound in the air or oxygen atmosphere utilized. For purposes of the present invention, the particularly preferred halogen is chlorine and it is highly recommended that the halogen compound utilized in this halogenation step be either hydrochloric acid or a hydrochloric acid producing substance. In particular, when the halogen component of the catalyst is chlorine, it is preferred to use a molar ratio of $H_2O$ to HCl of about 5:1 to about 100:1 during at least a portion of the oxidation step which follows the platinum group metal impregnation in order to adjust the final chlorine content of the catalyst to a range of about 0.1 to about 3.5 wt. %. Preferably, the duration of this halogenation step is about 1 to 5 or more hours.

A critical feature of the present invention involves subjecting the resulting oxidized, platinum group metal-oxide and silver-containing, and typically halogen-treated carrier material to a substantially water-free reduction step before the incorporation of the rhenium component by means of the rhenium carbonyl reagent. The importance of this reduction step comes from my observation that when an attempt is made to prepare the instant catalytic composite without first reducing the platinum group component, no significant improvement in the platinum-rhenium-silver catalyst system is obtained; put another way, it is my finding that it is essential for the platinum group component to be well dispersed in the porous carrier material in the elemental metallic state prior to incorporation of the rhenium component by the unique procedure of the present invention in order for synergistic interaction of the rhenium carbonyl with the dispersed platinum group metal to occur according to the theories that I have previously explained. Accordingly, this reduction step is designed to reduce substantially all of the platinum group component to the elemental metallic state and to assure a relatively uniform and finely divided dispersion of this metallic component throughout the porous carrier material. Preferably, a substantially pure and dry hydrogen stream (by use of the word "dry" I mean that it contains less than 20 vol. ppm. water and preferably less than 5 vol. ppm. water) is used as the reducing agent in this step. The reducing agent is contacted with the platinum group metal-oxide and silver-containing carrier material at conditions including a reduction temperature of about 450° F. to about 1200° F., for a period of about 0.5 to about 10 or more hours selected to reduce substantially all of the platinum group component to the elemental metallic state. Once this condition of finely divided dispersed platinum group metal in the porous carrier material is achieved, it is important that environments and/or conditions that could disturb or change this condition be avoided; specifically, I much prefer to maintain the freshly reduced carrier material containing the platinum group metal under a blanket of inert gas to avoid any possibility of contamination of same either by water or by oxygen.

A third essential ingredient of the present superactive catalytic composite is a rhenium component which I have chosen to characterize as a pyrolyzed rhenium carbonyl component in order to emphasize that the rhenium moiety of interest in my invention is the rhenium produced by decomposing a rhenium carbonyl in the presence of a finely divided dispersion of a platinum group metal and in the absence of materials such as oxygen or water which could interfere with the basic desired interaction of the rhenium carbonyl component with the platinum group metal component as previously explained. In view of the fact that all of the rhenium contained in a rhenium carbonyl compound is present in the elemental metallic state, an essential requirement of my invention is that the resulting reaction product of the rhenium carbonyl compound or complex with the platinum group metal- and silver-loaded carrier material is not subjected to conditions which could in any way interfere with the maintenance of the rhenium moiety in the elemental metallic state; consequently, avoidance of any conditions which would tend to cause the oxidation of any portion of the rhenium ingredient or of the platinum group ingredient is a requirement for full realization of the synergistic interaction enabled by the present invention. This rhenium component may be utilized in the resulting composite in any amount that is catalytically effective with the preferred amount typically corresponding to about 0.01 to about 5 wt. % thereof, calculated on an elemental rhenium basis. Best results are ordinarily obtained with about 0.05 to about 1 wt. % rhenium. The traditional rule for rhenium-platinum catalyst system is that best results are achieved when the amount of the rhenium component is set as a function of the amount of the platinum group component also holds for my composition; specifically, I find that best results with a rhenium to platinum group metal atomic ratio of about 0.1:1 to about 10:1, with an especially useful range comprising about 0.2:1 to about 5:1 and with superior results achieved at an atomic ratio of rhenium to platinum group metal of about 1:1.

The rhenium carbonyl ingredient may be reacted with the reduced platinum group metal- and silver-containing porous carrier material in any suitable manner known to those skilled in the catalyst formulation art which results in relatively good contact between the rhenium carbonyl complex and the platinum group component contained in the porous carrier material. One acceptable procedure for incorporating the rhenium carbonyl compound into the composite involves sublimating the rhenium carbonyl complex under conditions which enable it to pass into the vapor phase without being decomposed and thereafter contacting the resulting rhenium carbonyl sublimate with the platinum group metal- and silver-containing porous carrier material under conditions designed to achieve intimate contact of the carbonyl reagent with the platinum group metal dispersed on the carrier material. Typically, this procedure is performed under vacuum at a temperature of about 70° to about 250° F. for a period of time sufficient to react the desired amount of rhenium with the carrier material. In some cases, an inert carrier gas such as nitrogen can be admixed with the rhenium carbonyl sublimate in order to facilitate the intimate contacting of same with the platinum- and silver-loaded porous carrier material. A particularly preferred way of accomplishing this rhenium carbonyl reaction step is an impregnation procedure wherein the platinum- and silver-loaded porous carrier material is impregnated with a suitable solution containing the desired quantity of the rhenium carbonyl complex. For purposes of the present invention, organic solutions are preferred, although any suitable solution may be utilized as long as it does not interact with the rhenium carbonyl and cause decomposition of same. Obviously, the organic solution should be anhydrous in order to avoid detrimental interaction of water with the rhenium carbonyl compound. Suitable solvents are any of the commonly available organic solvents such as one of the available ethers, alcohols, ketones, aldehydes, paraffins, naphthenes and aromatic hydrocarbons, for example, acetone, acetyl acetone, benzylaldehyde, pentane, hexane, carbon tetrachloride, methyl isopropyl ketone, benzene, n-butyl ether, diethyl ether, ethylene glycol, methyl isobutyl ketone, diisobutyl ketone and the like organic solvents. Best results are ordinarily obtained when the solvent is acetone; consequently, the preferred impregnation solution is rhenium carbonyl dissolved in anhydrous acetone. The rhenium carbonyl complex suitable for use in the present invention may be either the pure rhenium carbonyl itself or a substituted rhenium carbonyl such as the rhenium carbonyl halides including the chlorides, bromides, and iodides and the like substituted rhenium carbonyl complexes. After impregnation of the carrier material with the rhenium carbonyl component, it is important that the solvent be removed or evaporated from the catalyst prior to decomposition of the rhenium carbonyl component by means of the hereinafter described pyrolysis step. The reason for removal of the solvent is that I believe that the presence of organic materials such as hydrocarbons or derivatives of hydrocarbons during the rhenium carbonyl pyrolysis step is highly detrimental to the synergistic interaction associated with the present invention. This solvent is removed by subjecting the rhenium carbonyl impregnated carrier material to a temperature of about 100° F. to about 250° F. in the presence of an inert gas or under a vacuum condition until substantially no further solvent is observed to come off the impregnated material. In the preferred case where acetone is used as the impregnation solvent, this drying of the impregnated carrier material typically takes about one half hour at a temperature of about 225° F. under moderate vacuum conditions.

After the rhenium carbonyl component is incorporated into the platinum- and silver-loaded porous carrier material, the resulting composite is, pursuant to the present invention, subjected to pyrolysis conditions designed to decompose substantially all of the rhenium carbonyl material, without oxidizing either the platinum group or the decomposed rhenium carbonyl component. This step is preferably conducted in an atmosphere which is substantially inert to the rhenium carbonyl such as in a nitrogen or noble gas-containing atmosphere. Preferably, this pyrolysis step takes place in the presence of a substantially pure and dry hydrogen stream. It is of course within the scope of the present invention to conduct the pyrolysis step under vacuum conditions. It is much preferred to conduct this step in the substantial absence of free oxygen and substances that could yield free oxygen under the conditions selected. Likewise, it is clear that best results are obtained when this step is performed in the total absence of water and of hydrocarbons and other organic materials. I have obtained best results in pyrolyzing rhenium carbonyl while using an anhydrous hydrogen stream at pyrolysis conditions including a temperature of about 300° F. to about 900° F. or more, preferably about 400° F. to about 750° F., a gas hourly space velocity of about 250 to about 1500 hr.$^{-1}$ for a period of about 0.5 to about 5 or more hours until no further evolution of carbon monoxide is noted. After the rhenium carbonyl component has been pyrolyzed, it is a much preferred practice to maintain the resulting catalytic composite in an inert environment (i.e. a nitrogen or the like inert gas blanket) until the catalyst is loaded into a reaction zone for use in the dehydrocyclization of hydrocarbons.

The resulting pyrolyzed catalytic composite may, in some cases, be beneficially subjected to a presulfiding step designed to incorporate in the catalytic composite from about 0.01 to about 1 wt. % sulfur calculated on an elemental basis. Preferably, this presulfiding treatment takes place in the presence of hydrogen and a suitable decomposable sulfur-containing compound such as hydrogen sulfide, lower molecular weight mercaptans, organic sulfides, etc. Typically, this procedure comprises treating the pyrolyzed catalyst with a sulfiding gas such as a mixture of hydrogen and hydrogen sulfide containing about 10 moles of hydrogen per mole of hydrogen sulfide at conditions sufficient to effect the desired incorporation of sulfur, generally including a temperature ranging from about 50° F. up to about 1000° F. It is generally a preferred practice to perform this presulfiding step under substantially water-free and oxygen-free conditions. It is within the scope of the present invention to maintain or achieve the sulfided state of the present catalyst during use in the dehydrocyclization of hydrocarbons by continuously or periodically adding a decomposable sulfur-containing compound, selected from the above-mentioned hereinbefore, to the reactor containing the superactive catalyst in an amount sufficient to provide about 1 to 500 wt. ppm., preferably about 1 to about 20 wt. ppm. of sulfur, based on hydrocarbon charge. According to another mode of operation, this sulfiding step may be accomplished during the pyrolysis step by utilizing a rhenium carbonyl reagent which has a sulfur-containing ligand or by adding H$_2$S to the hydrogen stream which is preferably used therein.

According to the present invention, the dehydrocyclizable hydrocarbon is contacted with the instant attenuated superactive acidic multimetallic catalyst in a dehydrocyclization zone maintained at dehydrocyclization conditions. This contacting may be accomplished by using the catalyst in a fixed bed system, a moving bed system, a fluidized bed system, or in a batch type operation; however, in view of the danger of attrition losses of the valuable catalyst and of well-known operational advantages, it is preferred to use either a fixed bed system or a dense-phase moving bed system such as is shown in U.S. Pat. No. 3,725,249. It is also contemplated that the contacting step can be performed in the presence of a physical mixture of particles of the catalyst of the present invention and particles of a conventional dual-function catalyst of the prior art. In a fixed bed system, the dehydrocyclizable hydrocarbon-containing charge stock is preheated by any suitable heating means to the desired reaction temperature and then passed into a dehydrocyclization zone containing a fixed bed of the attenuated superactive acidic multimetallic catalyst. It is, of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in a liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense-phase moving beds of the instant catalyst. In a multiple bed system, it is, of course, within the scope of the present invention to use the present catalyst in less than all of the beds with a conventional dual-function catalyst being used in the remainder of the beds. This dehydrocyclization zone may be one or more separate reactors with suitable heating means therebetween to compensate for the endothermic nature of the dehydrocyclization reaction that takes place in each catalyst bed.

Although hydrogen is the preferred diluent for use in the subject dehydrocyclization method, in some cases other art-recognized diluents may be advantageously utilized, either individually or in admixture with hydrogen, such as $C_1$ to $C_5$ paraffins such as methane, ethane, propane, butane and pentane; carbon dioxide, the like diluents, and mixtures thereof. Hydrogen is preferred because it serves the dual-function of not only lowering the partial pressure of the dehydrocyclizable hydrocarbon, but also of suppressing the formation of hydrogen-deficient, carbonaceous deposits (commonly called coke) on the catalytic composite. Ordinarily, hydrogen is utilized in amounts sufficient to insure a hydrogen to hydrocarbon mole ratio of about 0.1:1 to about 10:1, with best results obtained in the range of about 0.5:1 to about 5:1. The hydrogen stream charged to the dehydrocyclization zone will typically be recycled hydrogen obtained from the effluent stream from this zone after a suitable hydrogen separation step.

It is generally preferred to utilize the novel attenuated superactive acidic multimetallic catalytic composite in a substantially water-free environment. Essential to the achievement of this condition in the dehydrocyclization zone is the control of the water level present in the charge stock and the diluent stream which is being charged to the zone. Best results are ordinarily obtained when the total amount of water entering the conversion zone from any source is held to a level less than 50 ppm. and preferably less than 20 ppm. expressed as weight of equivalent water in the charge stock. In general, this can be accomplished by careful control of the water present in the charge stock and in the diluent stream. The charge stock can be dried by using any suitable drying means known to the art, such as a conventional solid adsorbent having a high selectivity for water, for instance, sodium or calcium crystalline aluminosilicates, silica gel, activated alumina, molecular sieves, anhydrous calcium sulfate, high surface area sodium, and the like adsorbents. Similarly, the water content of the charge stock may be adjusted by suitable stripping operations in the fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of $H_2O$ equivalent. In general, it is preferred to maintain the diluent stream entering the hydrocarbon conversion zone at a level of about 10 vol. ppm. of water or less and most preferably about 5 vol. ppm. or less. If the water level in the diluent stream is too high, drying of same can be conveniently accomplished by contacting this stream with a suitable desiccant such as those mentioned above.

The hydrocarbon dehydrocyclization conditions used in the present method include a reactor pressure which is selected from the range of about 0 psig. to about 250 psig., with the preferred pressure being about 50 psig. to about 150 psig. In fact, it is a singular advantage of the present invention that it allows stable operation at lower pressure than have heretofore been successfully utilized in hydrocarbon dehydrocyclization systems with all platinum monometallic catalysts. In other words, the attenuated superactive acidic multimetallic catalyst of the present invention allows the operation of a hydrocarbon dehydrocyclization system to be conducted at lower pressure for about the same or better catalyst cycle life before regeneration as has been heretofore realized with conventional monometallic catalysts at higher pressure.

The temperature required for dehydrocyclization with the instant catalyst is markedly lower than that required for a similar operation using a high quality catalyst of the prior art. This significant and desirable feature of the present invention is a consequence of the extraordinary activity of the acidic multimetallic catalyst of the present invention for the dehydrocyclization reaction. Hence, the present invention requires a temperature in the range of from 800° F. to about 1100° F. and preferably about 850° F. to about 1000° F. As is well known to those skilled in the dehydrocyclization art, the initial selection of the temperature within this broad range is made primarily as a function of the desired conversion level of the dehydrocyclizable hydrocarbon considering the characteristics of the charge stock and of the catalyst. Ordinarily, the temperature then is thereafter slowly increased during the run to compensate for the inevitable deactivation that occurs to provide a relatively constant value for conversion. Therefore, it is a feature of the present invention that not only is the initial temperature requirement substantially lower, but also the rate at which the temperature is increased in order to maintain a constant conversion level is substantially lower for the catalyst of the present invention than for an equivalent operation with a high quality dehydrocyclization catalyst which is manufactured in exactly the same manner as the catalyst of the present invention except for the inclusion of the pyrolyzed rhenium component. Moreover, for the catalyst of the present invention, the aromatic yield loss for a given temperature increase is substantially lower than for a high quality dehydrocyclization catalyst of the prior art.

The liquid hourly space velocity (LHSV) used in the instant dehydrocyclization method is selected from the range of about 0.1 to about 5 hr.$^{-1}$, with a value in the range of about 0.3 to about 2 hr.$^{-1}$ being preferred. In fact, it is a feature of the present invention that it allows operations to be conducted at higher LHSV than normally can be stably achieved in a dehydrocyclization process with a high quality dehydrocyclization catalyst of the prior art. This last feature is of immense economic significance because it allows a dehydrocyclization process to operate at the same throughput level with less catalyst inventory, or at greatly increased throughput level with the same catalyst inventory, than that heretofore used with conventional dehydrocyclization catalysts at no sacrifice in catalyst life before regeneration.

The following working examples are given to illustrate further the preparation of the attenuated superactive acidic multimetallic catalytic composite used in the present invention and the beneficial use thereof in the dehydrocyclization of hydrocarbons. It is understood that the examples are intended to be illustrative rather than restrictive.

These examples are all performed in a laboratory scale dehydrocyclization plant comprising a reactor, a hydrogen separating zone, heating means, cooling means, pumping means compressing means, and the like conventional equipment. In this plant, a feed stream containing the dehydrocyclizable hydrocarbon is combined with a hydrogen recycle stream and the resultant mixture heated to the desired conversion temperature, which refers herein to the temperature maintained at the inlet to the reactor. The heated mixture is then passed into contact with the instant attenuated superactive acidic multimetallic catalyst which is maintained in a substantially water-free environment and which is present as a fixed bed of catalyst particles in the reactor. The pressures reported herein are recorded at the outlet from the reactor. An effluent stream is withdrawn from the reactor, cooled, and passed into the hydrogen-separating zone wherein a hydrogen-containing gas phase separates from a hydrocarbon-rich liquid phase containing aromatic hydrocarbons, unconverted dehydrocyclizable hydrocarbons, and by-products of the dehydrocyclization reaction. A portion of the hydrogen-containing gas phase is recovered as excess recycle gas and the remaining portion is passed through a high surface area sodium scrubber and the resulting substantially water-free and sulfur-free hydrogen stream is recycled through suitable compressing means to the heating zone as described above. The hydrocarbon-rich liquid phase from the separating zone is withdrawn therefrom and subjected to analysis to determine conversion and selectivity for the desired aromatic hydrocarbon as will be indicated in the Examples. Conversion numbers of the dehydrocyclizable hydrocarbon reported herein are all calculated on the basis of disappearance of the dehydrocyclizable hydrocarbon and are expressed in weight percent. Similarly, selectivity numbers are reported on the basis of weight of desired aromatic hydrocarbon produced per 100 weight parts of dehydrocyclizable hydrocarbon charged.

All of the superactive acidic catalyst utilized in these examples are prepared according to the following general method with suitable modification in stoichiometry to achieve the compositions reported in each example. First, an alumina carrier material comprising 1/16-inch spheres having an apparent bulk density of about 0.5 g/cc is prepared by: forming an aluminum hydroxy chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel; aging, and washing the resulting particles with an ammoniacal solution and finally drying and calcining the aged and washed particles to form spherical particles of gamma-alumina containing about 0.3 wt. % combined chloride. Additional details as to this method of preparing the preferred gamma-alumina carrier material are given in the teachings of U.S. Pat. No. 2,620,314.

A first impregnation solution containing chloroplatinic acid and hydrogen chloride is then prepared. The alumina carrier material is thereafter admixed with the impregnation solution. The amount of the platinum reagent contained in this impregnation solution is calculated to result in a final composite containing a uniform dispersion of the hereinafter specified amounts of platinum. In order to insure uniform dispersion of the platinum component throughout the carrier material, the amount of hydrogen chloride used in this impregnation solution is about 2 wt. % of the alumina particles. This impregnation step is performed by adding the carrier material particles to the impregnation mixture with contant agitation. In addition, the volume of the solution is approximately the same as the bulk volume of the alumina carrier material particles so that all of the particles are immersed in the impregnation solution. The impregnation mixture is maintained in contact with the carrier material particles for a period of about $\frac{1}{2}$ to about 3 hours at a temperature of about 70° F. Thereafter, the temperature of the impregnation mixture is raised to about 225° F. and the excess solution is evaporated in a period of about 1 hour. The resulting dried platinum-impregnated particles are then subjected to an oxidation treatment in a dry air stream at a temperature of about 975° F. and a GHSV of about 500 hr.$^{-1}$ for about $\frac{1}{2}$ hour. This oxidation step is designed to convert substantially all of the platinum ingredient to the corresponding platinum oxide form. The resulting oxidized spheres are subsequently contacted in a halogen-treating step with an air stream containing $H_2O$ and HCl in a mole ratio of about 30:1 for about 2 hours at 975° F. and a GHSV of about 500 hr.$^{-1}$ in order to adjust the halogen content of the catalyst particles to a value of about 1 wt. %. The halogen-treated spheres are thereafter subjected to a second oxidation step with a dry air stream at 975° F. and a GHSV of 500 hr.$^{-1}$ for an additional period of about $\frac{1}{2}$ hour. The resulting oxidized, halogen-treated and platinum containing alumina particles are then subjected to a dry reduction step in order to reduce substantially all of the platinum component to the elemental metallic state. This platinum reduction step is performed by contacting the particles with a hydrocarbon-free, dry hydrogen stream at a temperature of 1050° F., atmospheric pressure, a GHSV of about 400 hr.$^{-1}$ and a contact time of about 1 hour.

A second aqueous impregnation solution containing silver nitrate is then prepared. The resulting platinum metal-containing alumina carrier material particles are thereafter admixed with this second impregnation solution. The amount of the silver reagent contained in this impregnation solution is calculated to result in a final composite containing the hereinafter specified amounts of silver. This second impregnation step is performed under a nitrogen blanket by adding the carrier material particles to the impregnation mixture with constant agitation. In addition, the volume of the solution is approximately the same as the bulk volume of the alumina carrier material particles so that all of the particles are immersed in the impregnation solution. The impregnation mixture is maintained in contact with the carrier material particles for a period of about 178 to about 3 hours at a temperature of about 70° F. Thereafter, the temperature of the impregnation mixture is raised to about 225° F. and the excess solution is evaporated in a period of about 1 hour. The resulting partially dried impregnated particles are then subjected to an additional drying step involving contacting with a dry nitrogen stream at a temperature of about 575° F. and a GHSV of about 500 hr.$^{-1}$ for about 178 hour. The resulting dried platinum- and silver-containing carrier material particles are then subjected to a dry reduction treatment designed to ensure that substantially all of the platinum component is reduced to the elemental metallic state and to maintain a uniform dispersion of this component in the carrier material. This second reduction step is accomplished by contacting the particles with a hydrocarbon-free, dry hydrogen stream containing less than 5 vol. ppm. H$_2$0 at a temperature of about 575° F., a pressure slightly above atmospheric, a flow rate of hydrogen through the particles corresponding to a GHSV of about 400 hr.$^{-1}$ and for a period of about one hour.

Rhenium carbonyl complex, Re$_2$(CO)$_{10}$, is thereafter dissolved in an anhydrous acetone solvent in order to prepare the rhenium carbonyl solution which was used as the vehicle for reacting rhenium carbonyl with the carrier material containing the uniformly dispersed platinum and silver. The amount of the complex used is selected to result in a finished catalyst containing the hereinafter specified amount of carbonyl-derived rhenium metal. The resulting rhenium carbonyl solution is then contacted under appropriate impregnation conditions with the reduced, platinum- and silver-containing alumina carrier material resulting from the previously described reduction step. The impregnation conditions utilized are: a contact time of about one half to about three hours, a temperature of about 70° F. and a pressure of about atmospheric. It is important to note that this impregnation step is conducted under a nitrogen blanket so that oxygen is excluded from the environment and also this step is performed under anhydrous conditions. Thereafter the acetone solvent is removed under flowing nitrogen at a temperature of about 175° F. for a period of about one hour. The resulting dry rhenium-carbonyl-impregnated particles are then subjected to a pyrolysis step designed to decompose the rhenium carbonyl component. This step involves subjecting the carbonyl impregnated particles to a flowing hydrogen stream at a first temperature of about 230° F. for about one half hour at a GHSV of about 600 hr.$^{-1}$ and at atmospheric pressure. Thereafter in the second portion of the pyrolysis step the temperature of the impregnated particles is raised to about 575° F. for an additional interval of about one hour until the evolution of CO is no longer evident. The resulting catalyst is then maintained under a nitrogen blanket until it is loaded into the reactor in the subsequently described dehydrocyclization test.

EXAMPLE I

The reactor is loaded with 100 cc of an attenuated superactive acidic catalyst containing, on an elemental basis, 0.375 wt. % platinum, 0.375 wt. % rhenium derived from rhenium carbonyl, 0.2 wt. % silver and about 1 wt. % chloride. This corresponds to an atomic ratio of rhenium to platinum of 1.05:1 and an atomic ratio of silver to platinum of 0.96:1. The feed stream utilized is commercial grade n-hexane. The feed stream is contacted with the catalyst at a temperature of 920° F., a pressure of 125 psig., a liquid hourly space velocity of 0.75 hr.$^{-1}$, and a hydrogen-containing recycle gas to hydrocarbon mole ratio of 4:1. The dehydrocyclization plant is lined-out at these conditions and a 20 hour test period commenced. The hydrocarbon product stream from the plant is continuously analyzed by GLC (gas liquid chromatography) and about a 90% conversion of n-hexane is observed with a selectivity for benzene of about 25%.

EXAMPLE II

The attenuated superactive acidic catalyst contains, on an elemental basis, 0.375 wt. % platinum, 0.5 wt. % rhenium derived from rhenium carbonyl, 0.25 wt. % silver and about 1 wt. % combined chloride. For this catalyst, the atomic ratio of rhenium to platinum is about 1.4:1 and the atomic ratio of silver to platinum is about 1.21:1. The feed stream is commercial grade normal heptane. The dehydrocyclization reactor is operated at a temperature of 900° F., a pressure of 125 psig., a liquid hourly space velocity of 0.75 hr.$^{-1}$, and a recycle gas to hydrocarbon mole ratio of 5:1. After a line-out period, a 20 hour test period is performed during which the average conversion of the n-heptane is maintained at about 95% with a selectivity for aromatics (a mixture of toluene and benzene) of about 45%.

EXAMPLE III

The acidic catalyst is the same as utilized in Example II. The feed stream is normal octane. The conditions utilized are a temperature of 880° F., a pressure of 125 psig., a liquid hourly space velocity of 0.75 hr.$^{-1}$, and a recycle gas to hydrocarbon mole ratio of 4:1. After a line-out period, a 20 hour test shows an average conversion of about 100% and a selectivity for aromatics of about 50%.

EXAMPLE IV

The acidic catalyst contains, on an elemental basis, about 0.25 wt. % platinum, about 0.25 wt. % rhenium derived from rhenium carbonyl, about 0.15 wt. % silver and about 1 wt. % combined chloride. On an atomic basis, the ratio of rhenium to platinum is 1.05:1 and the ratio of silver to platinum is 1.09:1. The feed stream is a 50/50 mixture of n-hexane and n-heptane. The conditions utilized are a temperature of 945° F., a pressure of 125 psig., a liquid hourly space velocity of 0.75 hr.$^{-1}$, and a recycle gas to hydrocarbon mole ratio of 5:1. After a line-out period, a 20 hour test is performed with a conversion of about 100% and a selectivity for aromatics of about 45%. The selectivity for benzene and toluene are about 20% and 25%, respectively.

It is intended to cover by the following claims, all changes and modifications of the above disclosure of the present invention which would be self-evident to a man of ordinary skill in the catalyst-formulation art or in the hydrocarbon dehydrocyclization art.

I claim as my invention:

1. A method for dehydrocyclizing a dehydrocyclizable hydrocarbon comprising contacting the hydrocarbon at hydrocarbon dehydrocyclization conditions with an acidic catalytic composite comprising a combination of a catalytically effective amount of a pyrolyzed rhenium carbonyl component with a porous carrier material containing catalytically effective amounts of a halogen component, a silver component and a uniform dispersion of a catalytically effective amount of a platinum group component maintained in the elemental metallic state.

2. A method as defined in claim 1 wherein the dehydrocyclizable hydrocarbon is admixed with hydrogen when it contacts the catalytic composite.

3. A method as defined in claim 1 wherein the platinum group component is platinum.

4. A method as defined in claim 1 wherein the platinum group component is iridium.

5. A method as defined in claim 1 wherein the platinum group component is palladium.

6. A method as defined in claim 1 wherein the platinum group component is rhodium.

7. A method as defined in claim 1 wherein the porous carrier material is a refractory inorganic oxide.

8. A method as defined in claim 7 wherein the refractory inorganic oxide is alumina.

9. A method as defined in claim 1 wherein the halogen is chlorine.

10. A method as defined in claim 1 wherein the acidic catalytic composite contains the components in amounts, calculated on an elemental basis, corresponding to about 0.01 to about 2 wt. % platinum group metal, about 0.01 to about 5 wt. % rhenium, about 0.01 to about 5 wt. % silver and about 0.01 to about 3.5 wt. % halogen.

11. A method as defined in claim 1 wherein substantially all of the silver component is present in the elemental metallic state.

12. A method as defined in claim 1 wherein the metals contents of the composite are adjusted so that the atomic ratio of silver to platinum group metal is about 0.01:1 to about 10:1 and the atomic ratio of rhenium to platinum group metal is about 0.1:1 to about 10:1.

13. A method as defined in claim 1 wherein the dehydrocyclizable hydrocarbon is an aliphatic hydrocarbon containing 6 to 20 atoms per molecule.

14. A method as defined in claim 13 wherein the aliphatic hydrocarbon is an olefin.

15. A method as defined in claim 13 wherein the aliphatic hydrocarbon is a paraffin.

16. A method as defined in claim 15 wherein the paraffin hydrocarbon is a paraffin containing 6 to 10 carbon atoms per molecule.

17. A method as defined in claim 15 wherein the paraffin is hexane.

18. A method as defined in claim 15 wherein the paraffin is heptane.

19. A method as defined in claim 15 wherein the paraffin is octane.

20. A method as defined in claim 15 wherein the paraffin is nonane.

21. A method as defined in claim 15 wherein the paraffin is a mixture of $C_6$ to $C_9$ paraffins.

22. A method as defined in claim 1 wherein the dehydrocyclizable hydrocarbon is contained in a naphtha fraction boiling in the range of about 140° F. to about 400° F.

23. A method as defined in claim 2 wherein the dehydrocyclization conditions include a temperature of about 800° to about 1100° F., a pressure of about 0 to about 250 psig., a LSHV of about 0.1 to about 5 $hr.^{-1}$, and a hydrogen to hydrocarbon mole ratio of about 0.1:1 to about 10:1.

24. A method as defined in claim 1 wherein the acidic catalytic composite contains, on an elemental basis, about 0.05 to about 1 wt. % platinum group metal, about 0.05 to about 1 wt. % rhenium, about 0.01 to about 1 wt. % silver and about 0.5 to about 1.5 wt. % halogen.

25. A method as defined in claim 1 wherein the contacting is performed in a substantially water-free environment.

* * * * *